(12) United States Patent
Eidenschink et al.

(10) Patent No.: US 9,788,842 B2
(45) Date of Patent: Oct. 17, 2017

(54) PMVR CLIP CONFIGURATIONS FOR MITRAL LEAFLET

(71) Applicant: St. Jude Medical, Cardiology Division, Inc., St. Paul, MN (US)

(72) Inventors: Tracee Eidenschink, Wayzata, MN (US); Melinda K. Kovach, Plymouth, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 533 days.

(21) Appl. No.: 14/198,032

(22) Filed: Mar. 5, 2014

(65) Prior Publication Data

US 2014/0257341 A1    Sep. 11, 2014

Related U.S. Application Data

(60) Provisional application No. 61/773,311, filed on Mar. 6, 2013.

(51) Int. Cl.
*A61B 17/122* (2006.01)
*A61B 17/128* (2006.01)
*A61B 17/00* (2006.01)

(52) U.S. Cl.
CPC ........ *A61B 17/122* (2013.01); *A61B 17/1285* (2013.01); *A61B 2017/00349* (2013.01)

(58) Field of Classification Search
CPC .. A61B 17/122; A61B 17/1285; Y10T 24/155
USPC ................ 606/139–143, 152–158, 200, 213; 623/1.24–1.28
See application file for complete search history.

(56) References Cited

U.S. PATENT DOCUMENTS

| | | | | |
|---|---|---|---|---|
| 3,908,662 A * | 9/1975 | Razgulov | ........... | A61B 17/1152 606/149 |
| 6,767,356 B2 * | 7/2004 | Kanner | ............. | A61B 17/0057 227/175.1 |
| 6,776,785 B1 * | 8/2004 | Yencho | ............. | A61B 17/0644 606/153 |
| 8,262,681 B1 * | 9/2012 | Gerrah | ................... | A61B 17/11 606/153 |
| 8,394,114 B2 * | 3/2013 | Schaller | ................ | A61B 17/11 606/142 |
| 8,758,397 B2 * | 6/2014 | Sibbitt, Jr. | ......... | A61B 17/0057 606/142 |
| 8,858,594 B2 * | 10/2014 | Clark | ................ | A61B 17/0057 606/155 |
| 2004/0039414 A1 * | 2/2004 | Carley | .............. | A61B 17/0057 606/213 |
| 2004/0087985 A1 * | 5/2004 | Loshakove | ........ | A61B 17/0057 606/153 |
| 2005/0080437 A1 * | 4/2005 | Wright | .............. | A61B 17/0644 606/153 |

(Continued)

*Primary Examiner* — David C Eastwood
*Assistant Examiner* — Charles Wei
(74) *Attorney, Agent, or Firm* — Lerner, David, Littenberg, Krumholz & Mentlik, LLP (57) ABSTRACT

A clip for leaflet tissue includes a substantially cylindrical hollow body having a proximal end and a distal end. In an initial configuration of the clip, the distal end has a diameter that is smaller than the diameter of the hollow body. The distal end is held in an expanded condition for delivery into a patient. When deployed, the distal end collapses to its initial configuration to grasp onto captured leaflet tissue.

12 Claims, 10 Drawing Sheets

(56) References Cited

U.S. PATENT DOCUMENTS

| | | | |
|---|---|---|---|
| 2007/0082021 A1* | 4/2007 | Bates | A61B 17/12022 |
| | | | 424/423 |
| 2010/0312259 A1* | 12/2010 | Houser | A61B 17/0057 |
| | | | 606/142 |
| 2012/0116427 A1* | 5/2012 | Raza | A61B 17/1155 |
| | | | 606/153 |
| 2012/0245603 A1* | 9/2012 | Voss | A61B 17/0057 |
| | | | 606/151 |
| 2012/0245606 A1* | 9/2012 | Goldberg | A61B 17/11 |
| | | | 606/153 |
| 2012/0283813 A1* | 11/2012 | Solem | A61F 2/91 |
| | | | 623/1.11 |

* cited by examiner

PMVR CLIP CONFIGURATIONS FOR MITRAL LEAFLET

CROSS-REFERENCE TO RELATED APPLICATIONS

This application claims the benefit of the filing date of the U.S. Provisional Patent Application No. 61/773,311, filed on Mar. 6, 2013, the disclosure of which application is hereby incorporated by reference in its entirety.

BACKGROUND OF THE INVENTION

The present disclosure is related to heart valve repair, and more particularly to devices, systems, and methods for transcatheter repair of a heart valve leaflet.

Properly functioning heart valves can maintain unidirectional blood flow in the circulatory system by opening and closing, depending on the difference in pressure on each side of the valve. The two atrioventricular valves (mitral and tricuspid valves) are multicusped valves that prevent backflow from the ventricles into the atria during systole. They are anchored to the wall of the ventricle by chordae tendineae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which one or more abnormal mitral valve leaflets invert into the atrium (i.e., a portion of the affected leaflet may be billowed, loose, and floppy). Furthermore, the chordae tendineae may stretch and thus become too long, or the chordae tendineae may be broken. As a result, the valve does not close normally, and the unsupported valve leaflet bulges back, or "prolapses," into the left atrium like a parachute. Thus, as the ventricle contracts, the abnormal leaflet may be propelled backwards, beyond its normal closure line into the left atrium, thereby allowing blood to flow back into the left atrium and the lungs.

Mitral valve prolapse causes mitral regurgitation. Isolated posterior leaflet prolapse of the human heart mitral valve, i.e., prolapse of a single leaflet, is the most common cause of mitral regurgitation. The exact cause of the prolapse is not clear. Untreated mitral regurgitation may lead to congestive heart failure and pulmonary hypertension.

Despite the various improvements that have been made to devices and methods for mitral valve leaflet repair, there remain some shortcomings. For example, conventional methods of treating mitral valve prolapse include replacement of the mitral valve, clipping the two mitral valve leaflets to one another, and resection of the prolapsed segment using open heart surgery. Such surgical methods may be invasive to the patient and may require an extended recovery period.

There therefore is a need for further improvements to the current techniques for treating heart valve leaflet prolapse. Among other advantages, the present disclosure may address one or more of these needs.

BRIEF SUMMARY OF THE INVENTION

According to an embodiment of the present disclosure, a clip for a leaflet tissue comprises a substantially cylindrical hollow body having a main portion, a proximal end portion and a distal end portion. The main portion has a diameter. The body has an initial configuration and a deployed configuration. The distal end portion in the initial configuration has a diameter less than the diameter of the main portion. The proximal end portion in the initial configuration has a diameter greater than the diameter of the main portion and in the deployed configuration has a diameter less than the main portion. In the deployed configuration, the main body is inverted relative to the initial configuration.

According to an embodiment of the present disclosure, a system for applying a clip to leaflet tissue comprises an elongated sheath, a rod disposed within the elongated sheath, and a clip disposed between the rod and the elongated sheath. The central rod has a hook at one end configured to releasably grasp to the leaflet tissue. The clip comprises a substantially cylindrical hollow body having a main portion, a proximal end portion and a distal end portion. The main portion has a diameter. The body has an initial configuration and a deployed configuration. The distal end portion in the initial configuration has a diameter less than the diameter of the main portion. The proximal end portion in the initial configuration has a diameter greater than the diameter of the main portion and in the deployed configuration has a diameter less than the main portion. In the deployed configuration, the main body is inverted relative to the initial configuration.

According to an embodiment of the present disclosure, a clip for a leaflet tissue comprises a substantially cylindrical hollow body and an edge portion extending from the body. The edge portion has a first configuration wherein the edge portion is configured to contract radially inwardly to have a diameter smaller than the diameter of the hollow body. The edge portion comprises a plurality of teeth configured to at least partially pierce and embed into a tissue.

BRIEF DESCRIPTION OF THE DRAWINGS

Various embodiments of the present disclosure will now be described with reference to the appended drawings. It is to be appreciated that these drawings depict only some embodiments of the disclosure and are therefore not to be considered limiting of the scope of the disclosure.

DETAILED DESCRIPTION

As used herein, the terms "proximal" and "distal" are to be taken as relative to a user (e.g., a surgeon or an interventional cardiologist) using the disclosed transcatheter devices. "Proximal" is to be understood as relatively close to the user and "distal" is to be understood as relatively farther away from the user. The invention will be described in connection with the repair of a mitral valve leaflet, but it may be useful in the repair of other types of cardiac valves or in the gathering and clamping of other types of loose body tissue.

Various embodiments of clips are described herein for grasping and holding a portion of tissue, for example, mitral valve leaflet tissue. While one or more exemplary embodiments of a delivery system for delivering and deploying the clips are described herein, the clips described herein may be deployed using other delivery systems as well. The description of an exemplary delivery system is not intended to limit the deployment of the clips to the described delivery system.

Figure 1A:
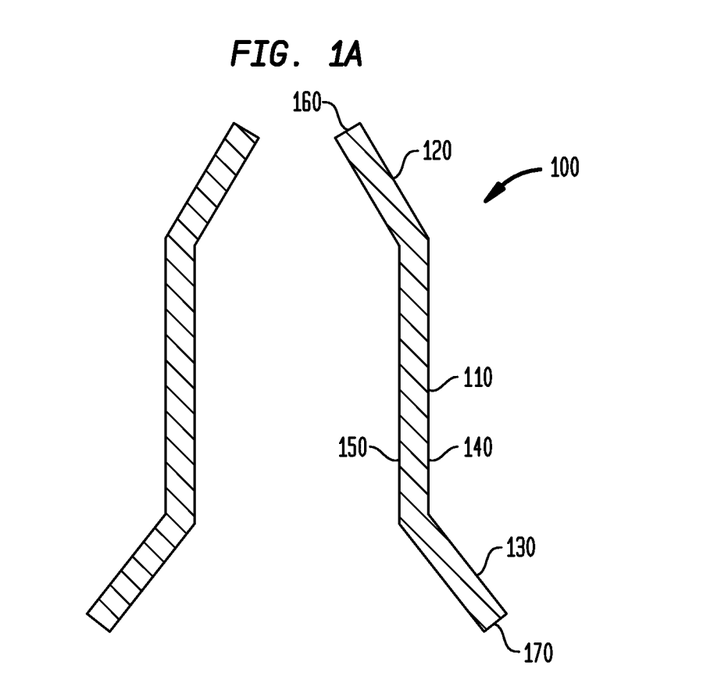
FIG. 1A is a longitudinal cross-sectional view of an invertible clip in its initial configuration, according to an embodiment of the present disclosure.
Figure 1B:
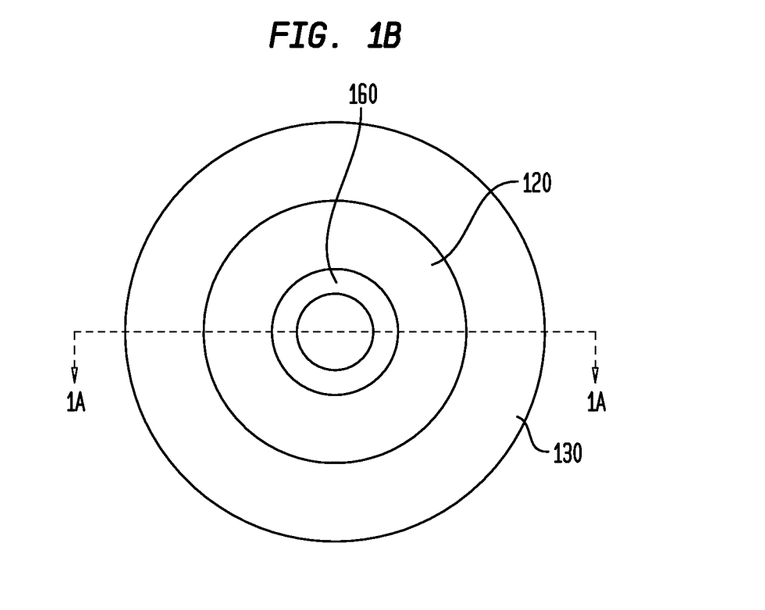
FIG. 1B is top view of the invertible clip of FIG. 1A in its initial configuration.

Referring now to FIGS. 1A and 1B, invertible clip 100 according to an embodiment of the disclosure is illustrated in a cross-sectional view and a top view, respectively. Clip 100 has generally cylindrical hollow body 110 with first surface 150, second surface 140, distal end 120 and proximal end 130. In its initial configuration, first surface 150 defines the inner surface of clip 100 and second surface 140 defines the outer surface of the clip. In the deployed configuration, however, clip 100 is inverted such that first surface 150 defines the outer surface of the clip while second surface 140 defines the inner surface of the clip, as will be described in more detail below.

Distal end 120 of clip 100 may include edge 160 configured to grasp and adhere to tissue, and proximal end 130 may include edge 170 similarly configured to grasp and adhere to tissue. For example, edges 160, 170 may be serrated or sufficiently sharp to at least partially pierce and embed into tissue. In the initial configuration of clip 100, distal end 120 tapers inwardly to a smaller diameter at edge 160 than the diameter of body 110, while proximal end 130 tapers outwardly to a larger diameter at edge 170 than the diameter of the body. For example, distal end 120 may taper to a diameter which is about 0% to about 50% smaller than the diameter of body 110, and proximal end 130 may taper to a diameter which is about 0% to about 25% larger than the diameter of the body. Distal end 120 and proximal end 130 are sufficiently flexible to deviate from their respective initial configurations upon application of an external force and may have diameters that are substantially the same as the diameter of body 110, for example, when mounted in a delivery apparatus.

Clip 100 may be made from a shape-memory material, such as a nickel/titanium alloy, or from Elgiloy® (a cobalt/chromium/Nickel "super-alloy") or a non-shape memory material like stainless steel. Distal end 120 of clip 100 may be heat treated, for example, to revert to its initial configuration in the absence of any external force acting thereupon. Body 110 may have a thickness of between about 0.003 inches (in.) and about 0.02 in., and an outer diameter of between about 5 millimeters (mm) and about 30 mm. Distal end 120 and proximal end 130 may have thicknesses that are about the same as the thickness of body 110. Alternatively, the thicknesses of distal end 120 and proximal end 130 may vary from the thickness of body 110, and may be about the same as or different from one another. By designing the clip with suitable thicknesses for distal end 120, proximal end 130, and body 110, clip 100 may be configured to be sufficiently strong to withstand fatigue after implantation and yet sufficiently flexible to invert as needed during the deployment. Clip 100 may have a length from about 2 mm to about 15 mm.

Figure 1C:
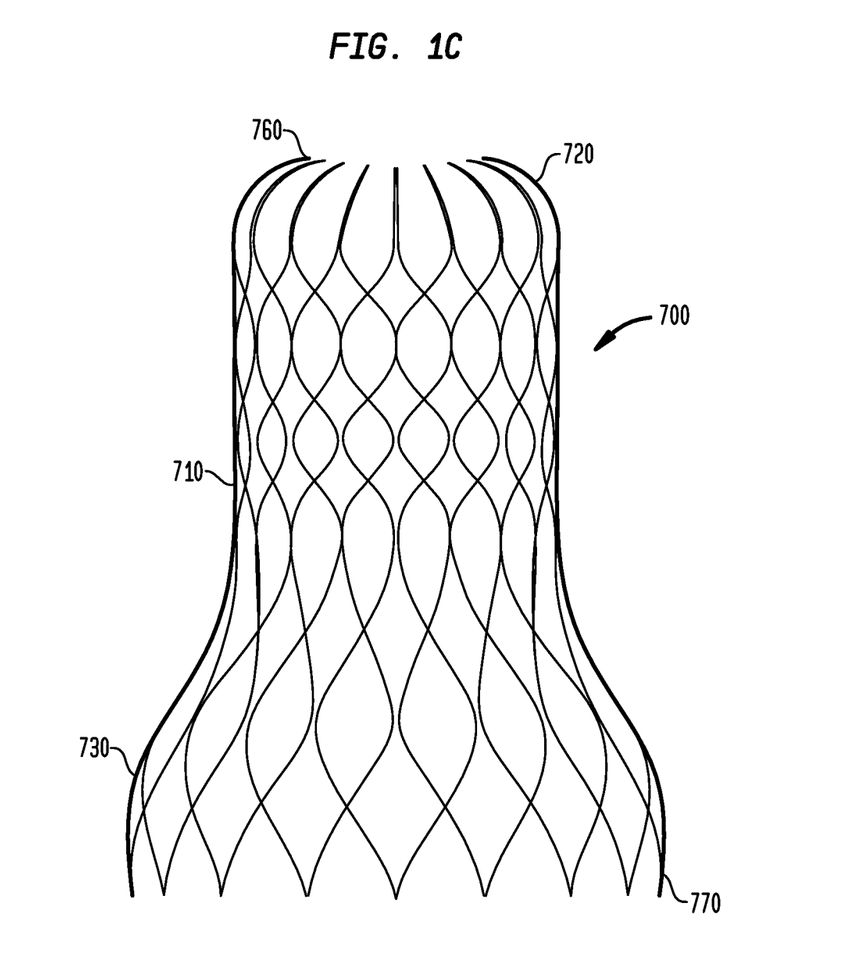
FIG. 1C illustrates an invertible clip in its initial configuration according to another embodiment of the disclosure.

Referring to FIG. 1C, clip 700 according to another embodiment of the disclosure is illustrated in a front view. Clip 700 comprises a braided configuration. In one configuration, clip 700 may comprise a single layer of braided wires. In other configurations, clip 700 may comprise two or more layers of braids. By way of a non-limiting example, clip 700 is braided from Nitinol wire. The Nitinol wire may have a diameter from about 0.005 in. to about 0.01 in. In an exemplary embodiment, distal end 720 may be heat set to taper inwardly, similar to distal end 120. Likewise, proximal end 730 may be heat set to taper outwardly, similar to proximal end 720. The dimensions of clip 700 may be similar to those described above with regard to clip 100. In one configuration, the braid ends at edges 760, 770 may be open and may embed into the tissue, thereby engaging clip 700 to the tissue, as described in further detail below.

Figure 2A:
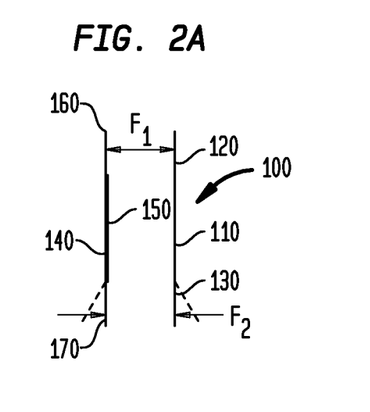
FIGS. 2A-2D schematically illustrate the stages of deployment of the invertible clips of FIGS. 1A and 1C.

The stages of deployment of invertible clips 100 and 700 will now be described briefly with reference to the schematic illustrations of FIGS. 2A-2E. During the first deployment stage, an external force $F_1$ (supplied by, for example, a component of the delivery apparatus described below) maintains distal end 120 of clip 100 in an expanded configuration relative to its initial relaxed configuration. Likewise, another external force $F_2$ (also supplied by, for example, a component of the delivery apparatus described below) maintains proximal end 130 of clip 100 in a contracted configuration relative to its initial relaxed configuration. As schematically illustrated in FIG. 2A, because of the respective forces $F_1$ and $F_2$, distal and proximal ends 120, 130 have generally the same diameter as body 110. In this first deployment stage, first surface 140 defines the outer surface of clip 100 and second surface 150 defines the inner surface of the clip.

Figure 2B:
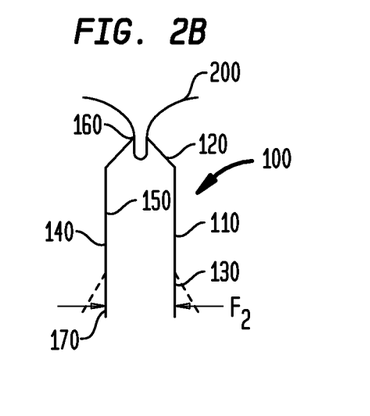

In the second deployment stage, depicted in FIG. 2B, removal of the external force $F_1$ (as described in detail below) causes distal end 120 of clip 100 to revert to its initial configuration by contracting radially due to, for example, the shape memory of the material of the clip. The contraction of distal end 120 causes edge 160 of the clip to at least partially pierce and embed into tissue 200 circumferentially. During this stage, the external force $F_2$ still maintains proximal end 130 of clip 100 in its contracted configuration relative to initial outward taper.

Figure 2C:
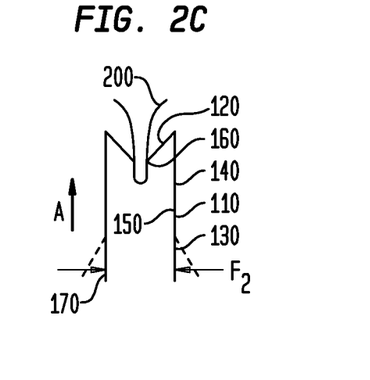
Figure 2D:
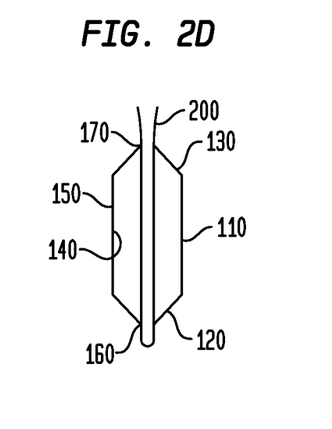

In the third stage of deployment, movement of the delivery apparatus (not shown) relative to tissue 200 causes clip 100 to move in the direction of arrow A, as illustrated in FIG. 2C. Edge 160 of clip 100 remains embedded in tissue 200 while distal end 120 begins to bend inwardly. As described in more detail below, either clip 100 may be pushed upwardly along with the delivery apparatus, thereby drawing tissue 200 into body 110, or tissue 200 may be pulled inwardly into the delivery apparatus by a component of the delivery apparatus. During this third stage, first surface 140 of clip 100 begins to transition from being the outer surface of the clip (i.e., facing away from captured tissue 200) to being the inner surface of the clip (i.e., facing towards captured tissue 200).

Figure 2E:
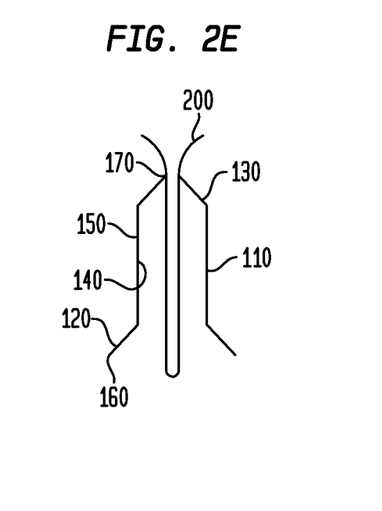
FIG. 2E schematically illustrates an alternative embodiment in the deployed state relative to FIG. 2D.

As the delivery apparatus continues to move relative to tissue 200, because edge 160 of clip 100 is embedded in the tissue, the delivery apparatus will also move relative to distal end 120 of the clip. However, proximal end 130 of clip 100 being constrained by the delivery apparatus will move along with the delivery apparatus, causing the clip to invert. As the deployment of clip 100 continues, the inversion of the clip continues until proximal end 130 thereof is no longer constrained by the delivery apparatus and reverts to its initial relaxed configuration. In the inverted state of clip 100, however, proximal end 130 contracts radially, rather than expanding radially. Edge 170 of proximal end 130 may at least partially pierce and embed into tissue 200. Inverted clip 100 is thus held to tissue 200 at both distal end 120 and proximal end 130, according to one embodiment of the invention. An alternative embodiment is illustrated schematically in FIG. 2E, wherein edge 160 of the distal end 120 is no longer engaged with tissue 200. Instead, distal end 120 flares outwardly away from the tissue due to, for example, the shape memory of the clip. In the embodiment of FIG. 2E, captured tissue 200 is maintained in the captured configuration only by proximal end 130. It will be further appreciated that a longer clip will capture a greater amount of tissue, in either of the embodiments of FIGS. 2D and 2E, and the length of the clip may be selected based on the amount of tissue to be captured.

Figure 3A:
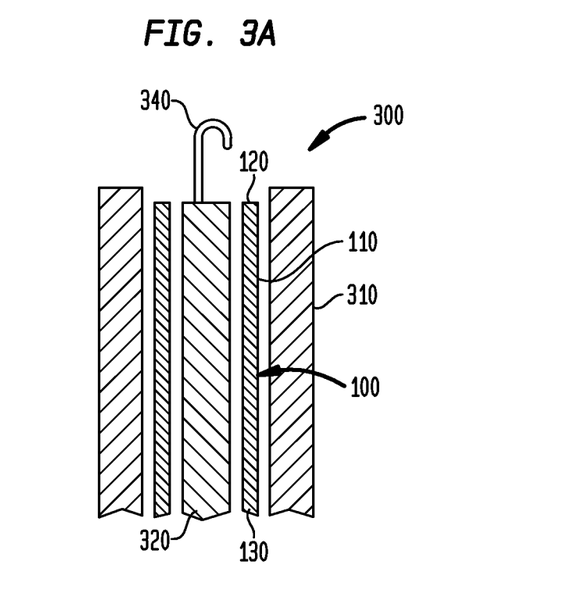
FIG. 3A is a partial longitudinal cross-sectional view of the clip of FIG. 1A disposed within a delivery system.

FIG. 3A schematically illustrates the distal portion of delivery apparatus 300 for delivering and deploying the clips of the present invention. Apparatus 300 includes elongated sheath 310 and rod 320 slidably disposed in the sheath. An invertible clip, such as clip 100 described above, is disposed between and is constrained by rod 320 and sheath 310. Rod 320 may include hook 340 at a distal end thereof. Hook 340 may serve to capture and pull tissue, for example, the tissue of a mitral valve leaflet.

Delivery apparatus 300 may be adapted to be inserted through the apex of a human heart so that the distal portion thereof may reach the patient's mitral valve to repair the same. Rod 320 is longitudinally slidable between a retracted position within elongated sheath 310 and a deployed position in which a distal tip of the central rod protrudes distally beyond the distal end of the sheath. Sheath 310 may be made of one or more echogenic materials so as to be more easily visualized inside a patient using three-dimensional echocardiography. Delivery apparatus 300 may further include a handle (not shown) at the proximal end of elongated sheath 310. The handle may have a plurality of actuators, for example, one for deploying and retracting rod 320 relative to sheath 310 and another for deploying and retracting the sheath relative to the rod.

The inner diameter of clip 100 may be generally about the same size as the outer diameter of central rod 320, while the outer diameter of the clip may be generally about the same size as the inner diameter of sheath 310. Thus, the radial gap between rod 320 and sheath 310 may be generally about equal to or only slightly larger than the wall thickness of clip 100. For example, for the clips having a wall thickness of between about 0.003 in. and about 0.02 in., the gap between rod 320 and sheath 310 may be about the same or slightly larger to allow for sliding movement between the various elements.

When clip 100 is mounted in delivery apparatus 300 between rod 320 and sheath 310, the rod deflects inwardly tapered distal end 120 of the clip from its initial relaxed configuration to an expanded configuration. In other words, rod 320 provides force $F_1$ described above with respect to FIG. 2A, to expand distal end 120 of the clip. If rod 320 is pulled away from distal end 120 of clip 100 or if the distal end of the clip is pushed away from the rod, the shape memory of the clip will cause the distal end to revert to its initial relaxed configuration.

Similarly, when clip 100 is mounted in delivery apparatus 300, sheath 310 constrains outwardly tapered proximal end 130 of the clip. That is, sheath 310 provides force $F_2$ described above with respect to FIG. 2A, to constrain proximal end 130 of the clip to a diameter about equal to the diameter of body 110, or at least less than the original diameter of proximal end 130. As sheath 310 is retracted from around proximal end 130 of clip 100 or as the proximal end of the clip is pushed out from the sheath, the shape memory of the clip causes the proximal end to revert to its initial relaxed configuration.

Figure 3B:
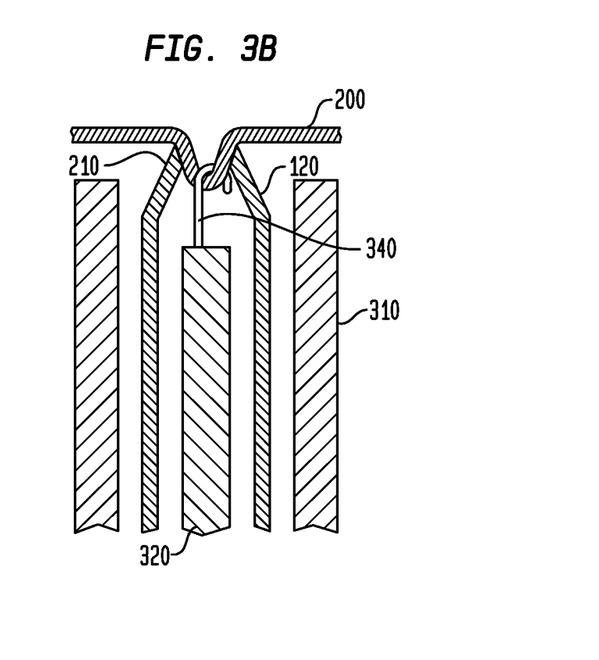
FIG. 3B is a partial longitudinal cross-sectional view similar to FIG. 3A, showing a first stage of deployment wherein leaflet tissue is being drawn into the delivery system.
Figure 3C:
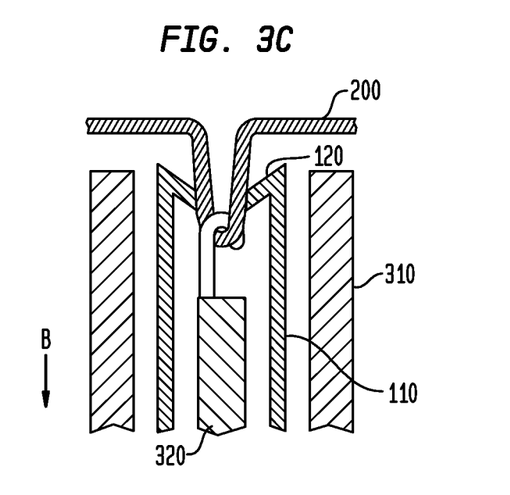
FIG. 3C is a partial longitudinal cross-sectional view similar to FIG. 3A, showing an intermediate stage of deployment wherein the clip begins to invert.

FIG. 3B illustrates the use of delivery apparatus 300 to capture leaflet tissue 200 and apply clip 100 to the captured tissue. As is known in the art, the distal end of delivery apparatus 300 along with clip 100 may be inserted into a patient, for example, through the apex of the heart into the left ventricle, so that distal end of the delivery apparatus is positioned adjacent a leaflet of the mitral valve. After positioning sheath 310 adjacent one side of the tissue, rod 320 is slid distally until hook 340 is positioned on the opposite side of the tissue. Rod 320 may then be retracted proximally, causing hook 340 to engage tissue 200 and pull the tissue towards and into sheath 310. As tissue 200 is drawn into sheath 310, it simultaneously is drawn into distal end 120 of clip 100. The movement of rod 320 further proximally away from distal end 120 of clip 100 frees the distal end to contract radially to its initial configuration, tightly engaging tissue 200 therein as it does so. Further proximal retraction of rod 320, as depicted by arrow B in FIG. 3C, pulls tissue 200 further into sheath 310. As distal end 120 of clip 100 is tightly engaged to tissue 200, the distal end moves along with the captured tissue, thereby commencing the inversion of the clip. As an alternative to retracting rod 320 proximally, sheath 310 and clip 100 may be moved distally relative to the rod, i.e., in the direction opposite that of arrow B, thereby achieving the same result.

Figure 3D:
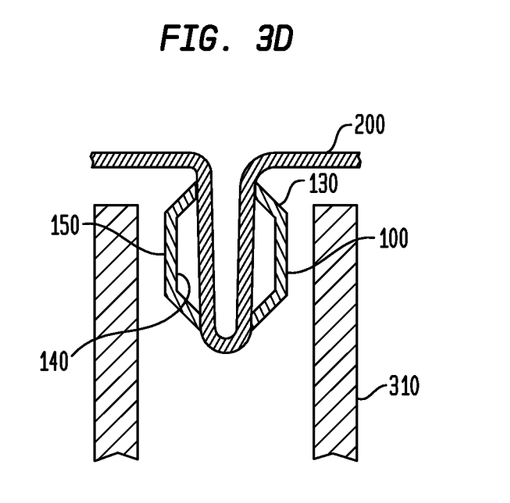
FIG. 3D is a longitudinal cross-sectional view similar to FIG. 3A, showing the clip the deployed stage.

FIG. 3D illustrates the deployed configuration of clip 100, wherein the clip has been inverted. First surface 140 now defines the inner surface of the clip facing captured tissue 200. Second surface 150, on the other hand, defines the outer surface facing away from captured tissue 200. Distal end 120 of clip 100 is now in a proximal position and proximal end 130 of clip 100 is now in a distal position. In the inverted configuration, proximal end 130 tends to contract radially relative to body 110. In an embodiment, distal end 120 may revert to its initial configuration, i.e., taper away from the tissue. In another embodiment, distal end 120 may remain engaged with tissue 200. When contracted, proximal end 130 may at least partially pierce and embed into tissue 200. Inverted clip 100 thus holds some of the loose and floppy leaflet tissue in a gathered configuration, thereby reducing or mitigating tissue prolapse. With clip 100 securely engaged with tissue 200, delivery apparatus 300, including rod 320 and sheath 310, may be withdrawn. For example, once clip 100 is securely engaged with tissue 200, sheath 310 may be withdrawn proximally from around the clip. Alternatively, clip 100, together with captured tissue 200, may be pushed out from the distal end of the sheath, for example, by rod 320. When the procedure has been completed, clip 100 remains in place in the patient.

Figure 4A:
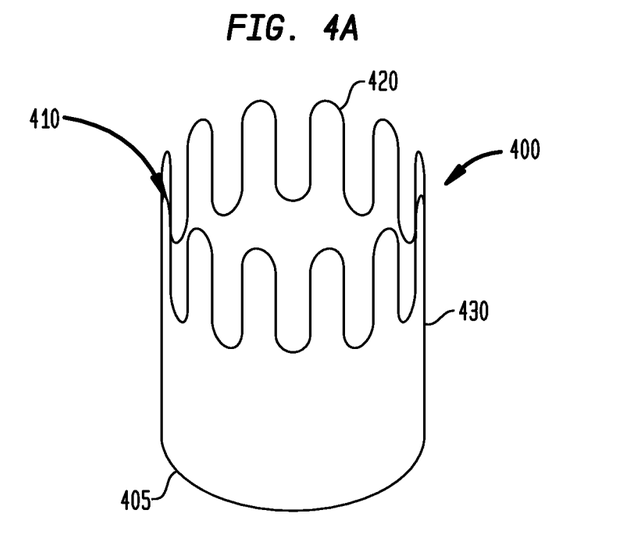
FIG. 4A is a perspective view of a clip according to another embodiment of the disclosure.
Figure 4B:
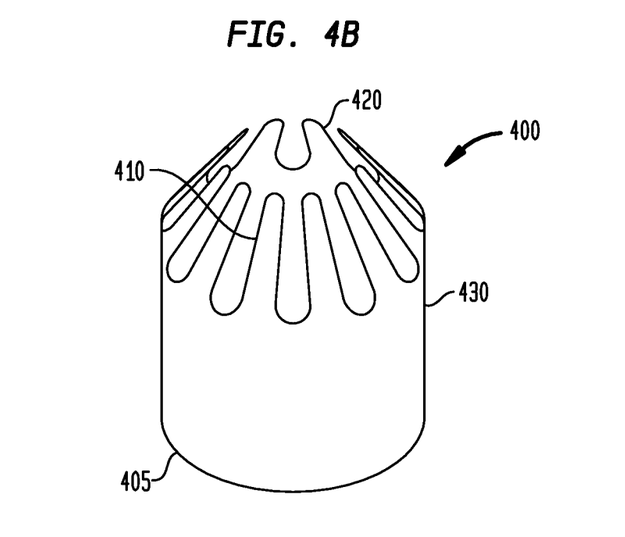
FIG. 4B is a perspective view of the clip of FIG. 4A in a deployed configuration.

Referring to FIGS. 4A-4B, clip 400 for gripping tissue according to an alternate embodiment of the disclosure is illustrated. Clip 400 has generally cylindrical body 430, proximal end 405 and distal end portion 410. Distal end portion 410 includes a plurality of teeth or serrations 420, which are biased to contract radially inward relative to cylindrical body 430 in an initial or relaxed configuration of the clip. A radially outward force exerted by, for example, a member disposed within clip 400 (not shown, but similar to the central rod 320 of FIG. 3A) may prevent distal end portion 410 from reverting to the relaxed configuration. Such member may be removed when a portion of tissue has been pulled into the distal end of clip 400. When the member has been removed, teeth or serrations 420 may bend inwardly, at least partially piercing into the tissue and securing clip 400 to the tissue. Thus, in addition to the inward radial force exerted by distal end portion 410 on the tissue, teeth or serrations 420 provide additional attachment to the tissue. Although clip 400 is described herein as having teeth or serrations 420 on the distal end 120 thereof, it will be appreciated that such teeth or serrations may also be provided on proximal end 130 of the clip, or on both the distal and the proximal ends of the clip.

Clip 400 may be made from Nitinol®, by way of a non-limiting example. Cylindrical body 430 may have a length between about 2 mm and about 15 mm, a diameter between about 5 mm and about 30 mm, and a wall thickness between about 0.003 in and about 0.02 in. Teeth or serrations 420 may have a length sufficient to penetrate tissue.

A delivery device similar to delivery apparatus 300 described above may be used to deliver and deploy clip 400 at a location adjacent a valve leaflet. The delivery device may be adapted to be inserted through the apex of a human heart so that a distal portion thereof may reach the patient's mitral valve to repair the same. Clip 400 may be disposed between an elongated sheath of the delivery device, such as sheath 310 of FIG. 3A, and a rod of the delivery device, such as rod 320 of FIG. 3A. The rod may serve to retain end portion 410 of clip 400 in a generally expanded configuration relative to its relaxed configuration. The distal end of the delivery device may be positioned in the vicinity of a mitral valve leaflet, and the delivery device may be operated in the same manner as delivery apparatus 300 to draw tissue of a leaflet into the distal end of the sheath and into clip 400. Once tissue has been pulled into clip 400, the movement of the rod relative to clip 400 enables end portion 410 of the clip to revert to its relaxed configuration, thereby collapsing radially inward and capturing the gathered tissue. With clip 400 secured to the leaflet tissue, the delivery device may be removed from the patient. The engagement of clip 400 on the gathered tissue reduces the loose and floppy tissue to mitigate tissue prolapse.

FIGS. 5A-5D schematically illustrate delivery device 500 for delivering various clips described herein, including clip 520 according to a still further embodiment of the present disclosure. Delivery device 500 includes sheath 510 and may further include a pusher (not shown) for pushing clip 520 away from sheath 510. Clips 520 may have a generally cylindrical ring 525 at one end, and a plurality of barbs 550 projecting from the ring toward the other end. Ring 525 may be fixed in size and thus not collapsible. On the other hand, barbs 550 may be separated from one another by slits 560, and may be formed so as to be biased radially inward in an initial relaxed condition. Each of slits 560 may have curved recess 540 at its end adjacent ring 525. Clip 520 is mounted on the outside of sheath 510 such that ring 525 circumscribes the sheath and barbs 550 are deflected outwardly along the sheath. It will be appreciated that curved recess 540 would lower the stresses induced in clip 520 when deployed.

Figure 5A:
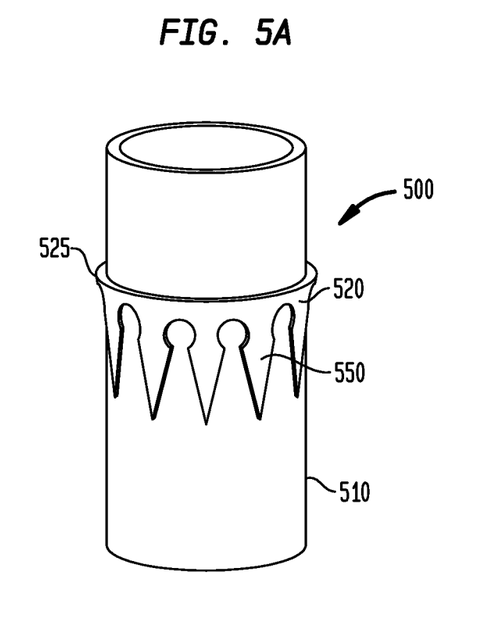
FIG. 5A is a perspective view of a clip according to yet another embodiment of the invention, installed on a delivery sheath.
Figure 5B:
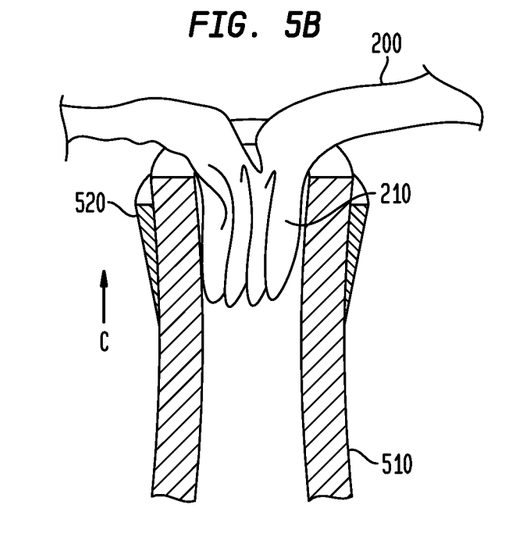
FIG. 5B is a longitudinal cross-sectional view of the clip of FIG. 5A in a first stage of deployment, wherein leaflet tissue has been drawn into the delivery sheath.
Figure 5C:
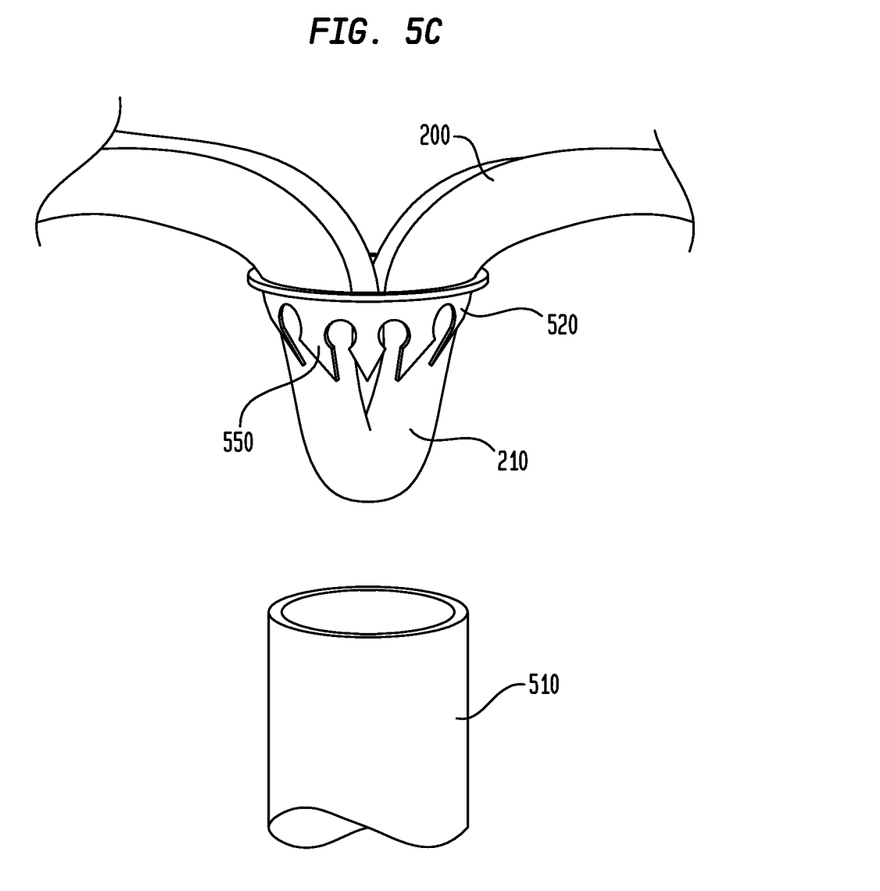
FIG. 5C is a side view of the clip of FIG. 5A in a deployed stage gripping the tissue.
Figure 5D:
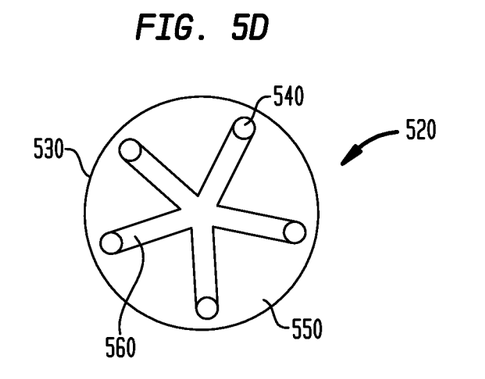
FIG. 5D is a top view of the clip of FIG. 5A in the deployed stage.

As illustrated in FIG. 5B, once portion 210 of leaflet tissue 200 has been drawn into sheath 510 (for example, with a member such as rod 320 of FIG. 3A), the pusher (not shown) is actuated to push clip 520 from sheath 510 onto tissue portion 210. In a preferred arrangement, the pusher may be in the form of a tubular shaft which may be slidable along the outer surface of sheath 510 to contact the outer periphery of clip 520 and push it off of the sheath. As clip 520 is pushed off of sheath 510, barbs 550 converge radially inwardly to their relaxed condition, thereby securing clip 520 to gathered tissue portion 210, as illustrated in FIG. 5C. Once clip 520 is secured to gathered tissue portion 210, delivery device 500 may be removed from the patient. The extent of loose and floppy leaflet tissue, and thus the ability of the leaflet tissue to prolapse, is thus reduced.

Figure 5E:
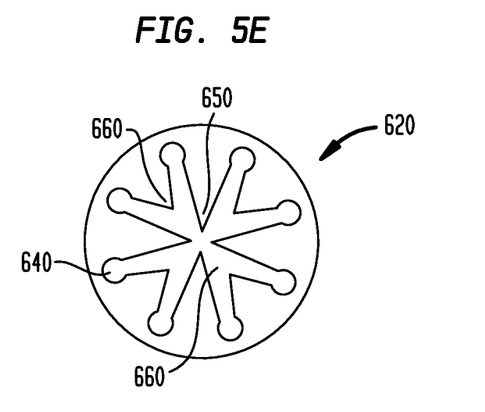
FIG. 5E is a top view of a clip according to a still further embodiment of the disclosure.

Referring now to FIG. 5E, clip 620 for a tissue leaflet is illustrated according to another embodiment of the disclosure. Clip 620 is generally similar to clip 520, except that clip 620 includes barbs 650, 660 that may have different lengths. An advantage of barbs 650, 660 having different lengths is that clip 620 can accommodate a tissue leaflet having varying tissue thicknesses and geometries, for example, from about 0.005 in. thick to about 0.08 in., which is the thickness range for healthy tissue. A diseased tissue will likely have higher thicknesses, which would be accommodated by clip 620 as well.

Although the disclosure describes particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A clip for leaflet tissue, the clip comprising:
a substantially cylindrical hollow body having a main portion, a first end portion and a second end portion, the main portion having a diameter, the body having an initial configuration and a use configuration, the second end portion in the initial configuration having a diameter less than the diameter of the main portion, the first end portion in the initial configuration having a diameter greater than the diameter of the main portion, and the first end portion in the use configuration having a diameter less than the diameter of the main portion, wherein the main body in the use configuration is inverted relative to the main body in the initial configuration, and
wherein the cylindrically hollow body comprises a braided configuration.

2. The clip according to claim 1, wherein the second end portion includes a plurality of fingers.

3. The clip according to claim 2, wherein the first end portion includes a plurality of fingers.

4. The clip according to claim 1, wherein the second end portion includes a serrated edge.

5. The clip according to claim 4, wherein the first end portion includes a serrated edge.

6. The clip according to claim 1, wherein the braided configuration comprises a Nitinol wire.

7. A system for applying a clip to leaflet tissue, the system comprising:
an elongated sheath;
a rod slidably disposed within the elongated sheath, the rod having a hook at one end configured to releasably grasp the leaflet tissue; and
a clip disposed between the rod and the elongated sheath, the clip including:
a substantially cylindrical hollow body having a main portion, a first end portion and a second end portion, the main portion having a diameter, the body having an initial configuration and a use configuration, the second end portion in the initial configuration having a diameter less than the diameter of the main portion, the first end portion in the initial configuration having a diameter greater than the diameter of the main portion, and the first end portion in the use configuration having a diameter less than the diameter of the main portion, wherein the main body in the use configuration is inverted relative to the main body in the initial configuration.

8. The system of claim 7, wherein the body further has a distorted configuration, the first end portion in the distorted configuration and the second end portion in the distorted configuration having diameters that are substantially the same as the diameter of the main body.

9. The system of claim 7, wherein the second end portion includes a plurality of fingers.

10. The system of claim 9, wherein the first end portion includes a plurality of fingers.

11. The system of claim 7, wherein the second end portion includes a serrated edge.

12. The system of claim 11, wherein the first end portion includes a serrated edge.

* * * * *